(12) United States Patent
Blaylock

(10) Patent No.: US 9,126,005 B1
(45) Date of Patent: Sep. 8, 2015

(54) ANESTHESIA BREATHING CIRCUIT TUBE SUPPORT

(76) Inventor: Rebecca C. Blaylock, Houston, TX (US)

( * ) Notice: Subject to any disclaimer, the term of this patent is extended or adjusted under 35 U.S.C. 154(b) by 215 days.

(21) Appl. No.: 13/452,869

(22) Filed: Apr. 21, 2012

(51) Int. Cl.
*F16M 13/00* (2006.01)
*A61M 16/08* (2006.01)
*A62B 18/08* (2006.01)

(52) U.S. Cl.
CPC .............. *A61M 16/08* (2013.01); *A62B 18/08* (2013.01)

(58) Field of Classification Search
CPC .............................. A61M 16/08; A61M 18/08
USPC ............................. 248/160, 161, 176.1, 205.3
See application file for complete search history.

(56) References Cited

U.S. PATENT DOCUMENTS

| | | | |
|---|---|---|---|
| 4,018,221 A | 4/1977 | Rennie | |
| 4,023,757 A | 5/1977 | Allard et al. | |
| 4,821,736 A | 4/1989 | Watson | |
| 5,147,322 A | 9/1992 | Bowen et al. | |
| 5,163,914 A | 11/1992 | Abel | |
| 5,672,159 A | 9/1997 | Warrick | |
| 6,375,017 B1 | 4/2002 | Schattner et al. | |
| 6,419,660 B1 | 7/2002 | Russo | |
| 6,718,571 B2 * | 4/2004 | Bartels | 5/81.1 R |
| 7,124,755 B2 | 10/2006 | Van Hooser | |
| 7,766,289 B2 | 8/2010 | Newkirk et al. | |
| 2004/0056159 A1 * | 3/2004 | Schulze | 248/125.1 |
| 2007/0170318 A1 | 7/2007 | Gunerman | |

OTHER PUBLICATIONS

SunMed, "Tube Tree"; http://www.sun-med.com/products/respiratory/tube-supports/metal/tube-tree-stainless-steel.
Bay-Medical, "Derbyshire Tube Support" http://www.bay-medical.com/products/equipment/tube-support/derbyshire-breathing-tube-support.html.
Trademark Medical, "Adjustable Tube Tree"; http://www.trademarkmedical.com/pro/pro-anesth-airway.html.
Baitella Ag, "FISSO® holding system"; http://www.baitella.com/pdf/FISSO_Anaesthesie_Intensivpflege_E.pdf.
Intersurgical Incorporated, "Knucklehead Mini"; http://us.intersurgical.com/products/system-accessories#tube-support.
JITTO International, "TANGO (TM) and ERGO (TM) Circuit Hangers"; http://www.jittointl.com/ergotango/.

* cited by examiner

*Primary Examiner* — Amy Sterling
(74) *Attorney, Agent, or Firm* — Kenneth A. Roddy

(57) ABSTRACT

A breathing tube support device for holding and supporting one or more flexible breathing tube(s) of a breathing circuit during provision of anesthesia, assisted and artificial ventilation and/or spontaneous ventilation has a flexible support arm formed of a length of flexible axially extendable and collapsible corrugated tubing, a mounting base at a bottom end thereof for attachment to the patient or a support surface, and a breathing tube holder a top end thereof for receiving and supporting a section of the breathing tube(s). The flexible support arm can be expanded to increase its length longitudinally and collapsed upon itself to shorten its length longitudinally, and is sufficiently flexible to assume a bent or curved configuration, and sufficiently stable to retain the bent or curved configuration, whereby breathing tube(s) held and supported by the device can be optimally positioned relative to the patient's head and neck area.

6 Claims, 3 Drawing Sheets

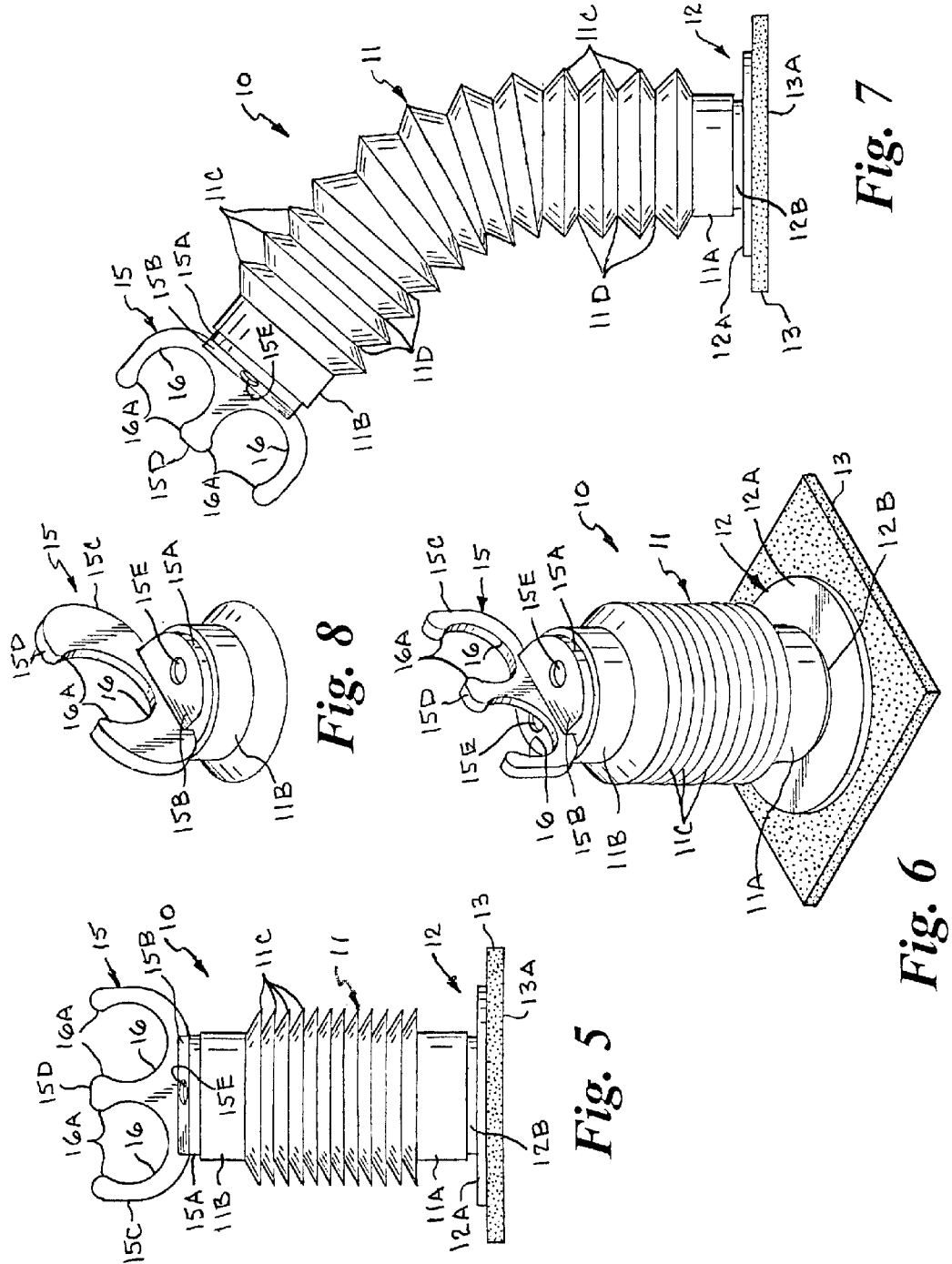

ANESTHESIA BREATHING CIRCUIT TUBE SUPPORT

BACKGROUND OF THE INVENTION

1. Field of the Invention

This invention relates generally to the field of medical devices and, more particularly to a breathing tube support device having a flexible support arm that is axially extendable and collapsible and capable of assuming a bent or curved configuration with a mounting base at a bottom end for attachment to a patient or support surface and a breathing tube holder member at a top end thereof for holding, supporting, and selectively positioning conventional flexible tubes or hoses of a breathing circuit during provision of anesthesia, assisted and artificial ventilation, and/or spontaneous ventilation.

2. Background Art

21 CFR §868.5240 (a) defines an "anesthesia breathing circuit" as a device that is intended to administer medical gases to a patient during anesthesia. It provides both an inhalation and exhalation route and may include a connector, adaptor, and Y-piece. 21 CFR §868.5280 (a) defines a "breathing tube support" as a device that is intended to support and anchor a patient's breathing tube(s).

Breathing circuits have been used in the anesthesia field for many years to provide a vehicle for transferring anesthesia gas from an anesthesia machine to a patient, and to transfer exhaled gas from the patient to the anesthesia machine. Currently, two primary types of breathing circuits are used. The first type is known as a "dual-limb" circuit. Such a device includes an expiratory tube and an inspiratory tube formed of flexible corrugated tubing that are usually connected to a Y-piece connector. The Y-piece is then coupled, at its patient end, to an endotracheal tube or an anesthesia face mask. The machine end of the inspiratory tube is coupled to the inspiratory port of either an anesthesia machine, or to a carbon dioxide absorber that is attached to an anesthesia machine. The machine end of the expiratory tube is attached to either the anesthesia machine, or to a carbon dioxide absorber attached to an anesthesia machine.

The other type of circuit is a "unilimb" circuit. A unilimb breathing circuit includes an expiratory tube and an inspiratory tube formed of flexible corrugated tubing, that are coupled in a coaxial relation, one inside the other. Usually, the inspiratory tube is disposed within the interior of the expiratory tube. A patient end connector is provided for coupling the patient end of the unilimb breathing circuit to either an endotracheal tube or an anesthesia face mask. The machine end of the unilimb circuit contains a coupler having an inspiratory coupler and a separate, expiratory coupler. The inspiratory coupler is coupled to the inspiratory port of a carbon dioxide absorber or anesthesia machine, and the expiratory coupler is coupled to the expiratory port of the anesthesia machine or carbon dioxide absorber. The inspiratory coupler handles gas from the inspiratory tube, and the expiratory coupler end handles gas from the expiratory coupler.

Both the inspiratory and expiratory tubes function in a similar manner. Anesthesia gas and oxygen are directed into the inspiratory tube, where the gases travel from the machine end of the inspiratory tube to the patient end. The gases are then inhaled by the patient. When the patient exhales, his or her expiratory gases flow into the expiratory tube, which conveys the gases back to the carbon dioxide absorber. The conventional breathing circuit may also include controls for assisting or controlling breathing, exhaled volume indicators, alarm systems, positive end expiratory pressure ("PEEP") valves, pressure indicators, gas concentration monitors, flow indicators, heated humidifiers for warming and humidifying the breathing gas.

The flexible corrugated breathing tubes of the breathing circuit extend from between the endotracheal tube of an intubated patient or an anesthesia face mask attached to the patient and the anesthesia machine, carbon dioxide absorber, or other apparatus which is typically disposed a distance away from the patient. It is important to insure that there are no kinks or bends in the breathing tubes.

The endotracheal tube placed in a patient's larynx and connected to the breathing circuit can cause more injury than is generally appreciated. Even brief incubation for surgical procedures may cause surface damage. Damage may occur wherever the endotracheal tube comes in contact with tissue although the larynx and trachea are particularly at risk. A minor area of insult may be followed by spontaneous resolution, or a devastating sequence of events leading to irreversible injury. During the presence of the endotracheal tube in the larynx, significant variables can affect the degree of insult, including tube size and shape, excessive cuff pressure, stylet trauma, infection, systemic disease, laryngopharyngeal reflux and the position of the endotracheal tube.

Movement of the endotracheal tube caused by manipulation of the surgeon during anesthesia, such as in a sitting shoulder operation, can cause shearing forces that add to the abrasion of the mucosa. Research studies have shown that excessive movement of the tube during assisted ventilation to further extend the damage caused by the endotracheal tube cuff. The tube position may be shifted during repositioning of the patient or by the operating surgeon. The endotracheal tube thus may be advanced against the tracheal wall or into the main bronchi or withdrawn into the larynx or hypopharynx. Other authors cite the vulnerability of the recurrent laryngeal nerve to pressure damage including from excessive stretching of the neck, among other causes, and that excessive head movement increases the pressure and shearing forces to which the arytenoids are exposed which further aggravates the inherent mucosal injury.

Some anesthesia providers do not support the breathing circuit tubing at all and allow the endotracheal tube and the breathing circuit tubing to dangle from the vocal cords. To minimize damage caused by the endotracheal tube, in a sitting operation, many anesthesia providers firmly affix the endotracheal tube to the patient and support the anesthesia breathing circuit tubes with a fixed tube tree, which is disposed on the unoperative side of the patient to minimize angulation and movement of the tube. A fixed tube tree typically has a flat horizontal leg and a flat vertical leg perpendicular thereto wherein the horizontal leg attaches to a support surface or slides under a bed or stretcher mattress or a pillow, and the outer end of the vertical legs are provided with cutout portions that hold the breathing circuit tubes.

However, when a surgeon pulls or manipulates a patient's shoulder, for example, the endotracheal tube and breathing circuit tubes secured on the tree will often pull on the larynx. The breathing circuit tubes secured on the tree will also exert a pulling force because the tree is typically disposed a distance from the patient. Head movement of the patient can also alter the position of the breathing circuit tubes.

There are several commercially available products and patents directed toward supports of various constructions for supporting breathing tubes and other medical tubing having various mounting arrangements.

SunMed, of Largo, Fla., manufactures several generally L-shaped breathing tube supports known a "Tube Tree" which have a flat horizontal leg and a flat vertical leg perpendicular thereto wherein the horizontal leg slides under a bed or stretcher mattress or a pillow, and the outer ends and lateral sides of the horizontal and vertical legs are provided with cutout portions that hold tubes of various diameters.

Bay-Medical, of Largo, Fla., markets an L-shaped breathing tube supports known as the "Derbyshire Tube Support" which has a flat horizontal leg and a flat vertical leg perpendicular thereto wherein the horizontal leg slides under a bed or stretcher mattress or a pillow, and the outer end of the vertical leg is provided with cutout portions that hold tubes of various diameters.

Trademark Medical, of Largo, Fla., markets an L-shaped Airway Circuit Holder known as an "Adjustable Tube Tree" which has a flat horizontal leg and a flat vertical leg perpendicular thereto with another flat vertical member pivotally and adjustably connected thereto which has cutout portions at its outer end that hold tubes of various diameters wherein the horizontal leg slides under a surgical pad or bed mattress, and the flat vertical member can be adjusted vertically and in a 180° arc.

Baitella AG. of Zurich, Switzerland, manufactures a FISSO® holding system which includes a pair of articulating arms connected by a central tightening unit which are positionable relative to one another and having ball and socket connections at their outer ends, one end of one arm is provided an operating table rail connector and the other arm is provided with a tube holder for holding breathing circuits, pressure transducers, endoscopes, instruments and other medical components and devices. The central tightening unit allows the arms and all joints to be fixed in place with a single knob.

JITTO International, of London, U.K., manufactures several breathing tube circuit holders or hangers under the brand name TANGO™ and ERGO™ Circuit Hangers that have articulating arms mounted in either of a wall mount cradle, pole clamp, rail clamp or table clamp with a flexible arm at the outer end thereof which can be adjusted to variable rotational angles and a multiple tube holder at the outer end of the flexible arm for supporting breathing circuit tubes of different diameters.

Gunerman, U.S. Published Patent Application 2007/0170318, assigned to Intersurgical Incorporated, of Liverpool, N.Y., discloses a breathing tube support arm for supporting a patient's breathing tube(s) which includes a system of hollow, interlocking, articulating beads, and a system of stiffeners inside of the hollow beads, the stiffeners being of three different stiffnesses. The support arm has a universal rail mounting block at the base end, and a tube holder or connector at a top end for receiving the breathing tube(s). Intersurgical Incorporated also markets a version known as the "Knucklehead Mini" which has a flat or L-shaped base member.

Newkirk et al, U.S. Pat. No. 7,766,289 discloses a line management device for supporting one or more patient care lines adapted to extend from a patient supported on a bed. The device includes a flexible support body, a coupler at one end to couple the support body to the bed, and a line manager at the other end, the line manager including a body, a plurality of upwardly extending fingers extending from the body, at least one of the upwardly extending fingers and a plurality of channels located between the upwardly extending fingers.

Van Hooser, U.S. Pat. No. 7,124,755 discloses a support arm for use in a respiratory circuit that includes a plurality of arm segments movably connected with one another such that the arm segments are adjustable with respect to another. At least one inflatable bladder is operably disposed at a point of connection between at least two of the arm segments. The arm segments are locked into position with respect to one another upon inflation of the bladder. The arm segments are released and positionable with respect to one another upon deflation of the bladder. Also, a respiratory support member is attached to one of the arm segments. The respiratory support member is configured for engaging the respiratory circuit to support the respiratory circuit.

Schattner et al, U.S. Pat. No. 6,375,017 discloses a tubing organizer apparatus which includes a body member that extends radially outwardly from a central axis. The body member has opposite surfaces and a peripheral wall that is disposed between the opposite surfaces. The peripheral wall includes a plurality of exterior wall segments facing outwardly relative to the central axis and a plurality of interior wall segments connected to the exterior wall segments that are configured to form a corresponding plurality of notches extending inwardly between consecutive ones of the exterior wall segments and into the body member relative to the central axis. The tubing organizer apparatus may also include a generally L-shaped support structure for rotatably mounting the body member thereto, and may include a plurality of gates, each gate spanning across a respective notch for releasably retaining one or more lengths of pliable tubing within the respective notch.

Allard et al, U.S. Pat. No. 4,023,757 discloses a holder for removable attachment to a hospital bed for releasably holding control devices operated by the patient. The holder includes an elongated flexible and positionable member attachable at one end to the frame of the bed and having a head at the other end formed with slotted openings for receiving electrical and other types of cords or tubular hoses.

Abel, U.S. Pat. No. 5,163,914 discloses a respirator hose support pad for tracheostomy patients that has a hook and loop fastener structure on the central bottom surface for releasable attachment to a patient's garment in the upper central chest area. The terminal oppositely disposed ends of the pad each have an extending flange that serve as handles. The pad additionally has a detachable flexible belt on the top surface for adjustable loose securement of the respirator hose onto the top of the pad such that the hose is loosely retained between the pad and belt, and may slide back and forth across the pad to prevent excessive pulling on the tracheostomy tube as the patient moves. The interior of the pad contains a compressible and somewhat resilient padding material to dampen the irritating and painful effect on the patient's tracheostomy of the respirator hose vibrations and jerking movements caused by the intermittent positive pressure introduction of gasses into the patient. The pad is additionally utilized to help maintain the respirator hose angling downhill in order to direct fluids which naturally condense in the respirator hose away from the patient's tracheostomy tube and lungs.

Warrick, U.S. Pat. No. 5,672,159 discloses a medical tubing support which includes a harness strap that is attached around the body of a patient, a detachable pad selectively attached to the harness strap, and at least one adjustable strap pivotally attached to the detachable pad which secures ventilation circuit tubing on the detachable pad. The first end of the adjustable strap is attached to a rivet located in the center of the detachable pad to allow pivotal movement, and the second end of the adjustable strap is wrapped over an object such as ventilation circuit tubes to hold the tubes on the detachable pad. Hook and loop surfaces disposed between the detachable pad and the adjustable strap enables the adjustable strap to be selectively fixed in position on the detachable pad, and hook and loop surfaces provided between the detachable pad and the topside of the harness allows the detachable pad to be selectively placed on the topside of the harness.

Rennie, U.S. Pat. No. 4,018,221 discloses a support for anesthetic gas delivery hoses and endotracheal tubes comprising an enlongated flexible strap with opposite sides of opposite ends of the strap provided with strips of hook and loop fasteners secured thereto. One of the fastener strips is spaced from the corresponding terminal end of the strap and that terminal end has a thick somewhat flexible and deformable pad secured thereto on the same side as the adjacent fastener strip. The strap may be encircled about a portion of a patient's body, such as the patient's head, and the opposite end portions of the strap may be overlapped with the fastener strips engaged with each other securing the strap about the patient's head. The overlapped portions of the pad and opposite end portion of the strap define opposing friction surfaces between which anesthesia hoses, etc., may be clamped for stationary support from the patient's head.

Watson, U.S. Pat. No. 4,821,736 discloses a head-mounted device for supporting breathing circuit tubes and $CO_2$ sensor which positions the sensor and breathing tubes adjacent the centerline of the forehead and above the head. The device includes a cushion positionable on the forehead, a rigid plate positionable over the cushion and having first and second portions, a band wrapped around the outer surfaces of the first plate portion and cushion and around the head, and connecting means on the second plate portion and sensor for attaching the sensor and breathing circuit tubes adjacent the centerline of the forehead and above the head. The plate counterbalances the weight of the sensor and provides a thermal shield protecting the patient from heat generated by the sensor.

Russo, U.S. Pat. No. 6,419,660 discloses a tube holder which includes a base for attachment to a surface, for example, a patient's skin, and a tab for securing the tube to the base. In one embodiment, the tube holder includes a first layer having first and second sides and first and second sections, and a second layer having first and second sides and first and second sections. The first sides of the first and second layers are attached to one another in the first sections of the first and second layers, the second sections of the first sides of the first and second layers are unattached to one another, and the first sections of the first and second layers form the tab and the second sections form the base. The tube holder also includes a third layer attached to the second side of the first layer for receiving a tube.

Bowen et al, U.S. Pat. No. 5,147,322 discloses a medical appliance securing device for laterally and longitudinally securing generally tubular members having various diameters to any desired location on the surface of a patient's skin or other support. The appliance comprises an anchoring patch having one surface coated with adhesive for bonding the device to a patient's skin or some other support, and a retaining tab connected to the anchoring patch that contains an aperture such that the retaining tab may be wrapped around the circumference of the tubular member, inserted through the aperture, and firmly secured to the anchoring patch through the use of fastening means.

SUMMARY OF THE INVENTION

The present invention overcomes the aforementioned problems, and is distinguished over the prior art in general, and these patents in particular by a breathing tube support device that attaches to a patient or optionally to a support surface for holding, supporting, and selectively positioning conventional flexible tubes or hoses of a breathing circuit during provision of anesthesia, assisted and artificial ventilation, and/or spontaneous ventilation. The breathing tube support device has a flexible support arm formed of a length of flexible axially extendable and collapsible corrugated tubing, a mounting base at a bottom end thereof for attachment to the patient or support surface, and a breathing tube holder member at a top end thereof for receiving and supporting a section of the flexible breathing tube(s) of the breathing circuit. The flexible support arm can be expanded to increase its length longitudinally and collapsed upon itself to shorten its length longitudinally, and is sufficiently flexible to assume a bent or curved configuration, and sufficiently stable to retain the bent or curved configuration, whereby flexible breathing tube(s) of the breathing circuit held and supported by the device can be optimally positioned relative to the patient's head and neck area. The mounting base may have a flexible peel and stick foam pad on an underside sized and shaped and sufficiently flexible to conform to and adhere to the patient's shoulder or other body surface or to a support surface.

One of the significant features and advantages of the present breathing tube support device is that it supports one or more tubes of a conventional breathing circuit and has a flexible arm that can be extended (lengthened) and collapsed (shortened) longitudinally upon itself in an accordion-like manner and is capable of assuming a bent or curved configuration and retaining that configuration until positioned into another bent, curved, or straight configuration, thus allowing an anesthesia provider to selectively adjust and optimally position the breathing tubes of the breathing circuit relative to a patient's head and neck area, and to accommodate a wide range of patient sizes, patient mobility, head movement, and medical procedures, etc.

Another significant feature and advantage of the present breathing tube support device is that it has a mounting base at the bottom end of the flexible arm with a peel and stick cushioning pad on the underside that can be adhered to a patient's shoulder between the neck and the outer portion of the shoulder joint, or other location on the patient's body, or to a support surface, to accommodate the movement of an intubated patient, while maintaining relative position of the breathing tubes regardless of the position of the patient.

Another feature and advantage of the present breathing tube support device is that it allows an anesthesia provider to selectively adjust and optimally position the breathing tubes to minimize forces applied to an endotracheal tube and the risk of injury to the intubated patient.

A still further feature and advantage of the present breathing tube support device is that it is simple in construction, inexpensive to manufacture, and rugged and reliable in operation.

Other features and advantages of the invention will become apparent from time to time throughout the specification and claims as hereinafter related.

The above and further features and advantages of the present invention will best be understood by reference to following drawings taken in conjunction with the following specification.

BRIEF DESCRIPTION OF THE DRAWINGS

FIGS. 5 and 6 are a side elevation view, and a perspective view, respectively, of the breathing tube support showing the flexible arm in longitudinally collapsed (shortened) condition.

FIG. 7 is a side elevation view of the breathing tube support showing the flexible arm in a bent or curved condition.

FIG. 8 is a perspective view of a tube holder member of the breathing tube support showing a single keyhole slot.

DESCRIPTION OF THE PREFERRED EMBODIMENT

Figure 1:
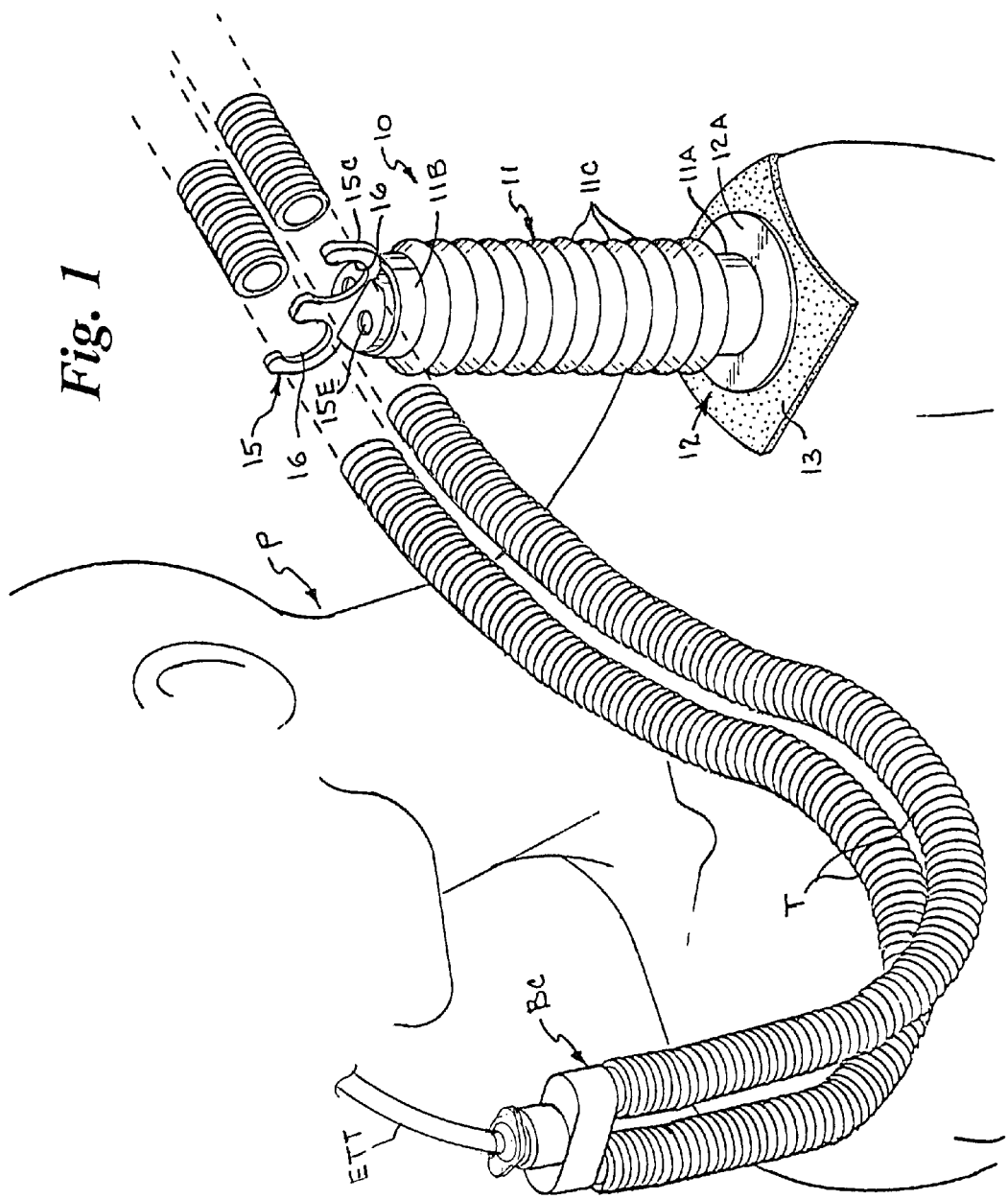
FIG. 1 is a pictorial view showing a breathing tube support in accordance with the present invention adhered to a patient's shoulder and supporting a pair of breathing tubes of a conventional dual-limb breathing tube circuit.
Figure 4:
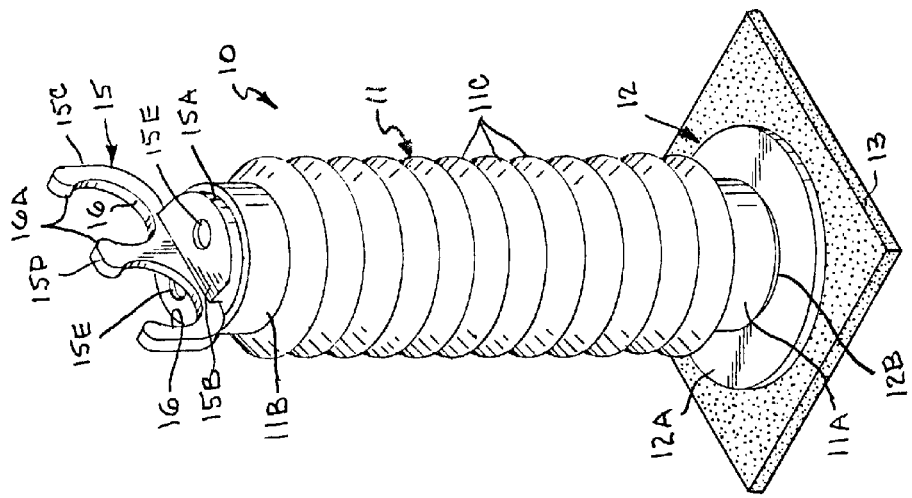
FIG. 4 is a perspective view of the breathing tube support showing the flexible arm in a longitudinally extended (lengthened) condition.
Figure 2:
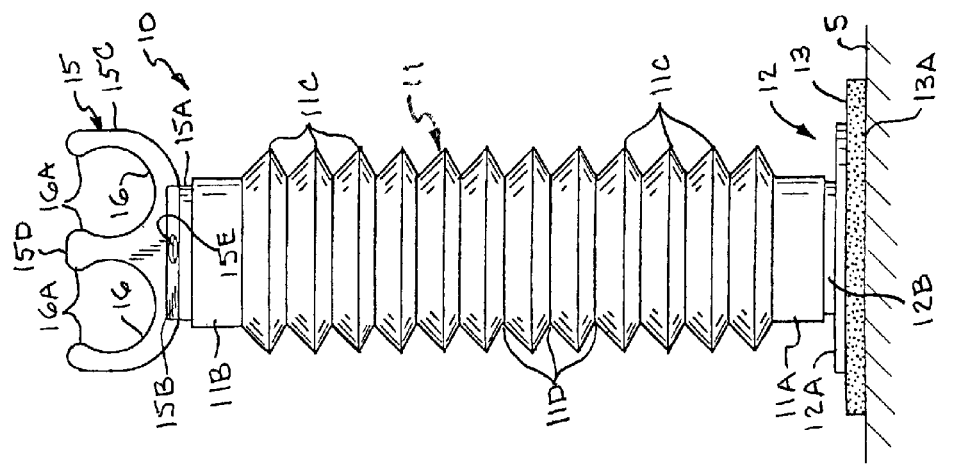
FIG. 2 is a side elevation view, of the breathing tube support showing the flexible arm in a longitudinally extended (lengthened) condition.

Referring now to the drawings by numerals of reference, and particularly to FIG. 1, the present breathing tube support device 10 attaches to a patient or other support surface for holding, supporting, and selectively positioning conventional flexible tubes or hoses T of a breathing circuit BC during provision of anesthesia, assisted and artificial ventilation, and/or spontaneous ventilation. For purposes of example only, and not limited thereto, the breathing tube support device 10 is shown in FIG. 1 attached to a patient P and the exemplary breathing circuit BC shown is a "dual-limb" circuit which includes an expiratory tube and an inspiratory tube formed of flexible corrugated tubing that are coupled at the patient end to a conventional endotracheal tube ETT, a portion of which is shown. The other end of the flexible tubes or hoses T of the breathing circuit BC are connected in a conventional manner to an anesthesia machine (conventional and therefore not shown). FIG. 2 shows the present breathing tube support device 10 attached to a support surface S.

Referring additionally to FIGS. 2 through 7, the preferred breathing tube support device 10 includes a tubular support arm 11 formed of axially extendable and collapsible corrugated tubing having a tubular first end portion 11A at a first end, and a tubular second end portion 11B at an opposed second end. A mounting base 12 is secured to the tubular first end portion 11A of the support arm 11, and a tube holder member 15 is secured to the tubular second end portion 11A of the support arm.

In a preferred embodiment, the tubular support arm 11 is an elongate configuration and formed of axially extendable and collapsible corrugated plastic tubing of the type having an accordion-like construction of ridges and folds represented by the numerals 11C and 11D, respectively, along the length thereof between the tubular first and second end portions 11A and 11B. The extendable and collapsible corrugated tubing of accordion-like construction is generally known in the art and is capable of assuming any bent or curved configuration selected by the anesthesiologist or other medical personnel and is sufficiently stable to retain that configuration until positioned into another bent, curved, or straight configuration. This tubing is also capable of being extended (lengthened) and collapsed (shortened) longitudinally upon itself in an accordion-like effect by virtue of the ridges and folds. Suitable accordion-like extendable and collapsible corrugated plastic tubing material for use in making the present flexible support arm 11 is available from a number of manufacturers such as, for example, GlobalMed Inc., of Ontario, Canada, and King Systems Corporation, of Noblesville, Ind.

FIGS. 1-4 show the tubular support arm 11 of the breathing tube support device 10 in a longitudinally expanded (lengthened) condition, and FIGS. 5 and 6 show the support arm in a longitudinally collapsed (shortened) condition, respectively. In a preferred embodiment, but not limited thereto, the length of the tubular support arm 11 may be about 6 cm (about 2.4 inches) in the collapsed condition, and expandable to extend to about 18 cm (about 7.1 inches) in length. FIG. 7 shows the tubular support arm 11 of the breathing tube support 10 in a bent or curved configuration.

In the illustrated exemplary embodiment, the mounting base 12 has a generally circular bottom flange 12A with a reduced diameter tubular neck portion 12B extending vertically upward therefrom. The tubular neck portion 12B is sized to be received in the tubular first end portion 11A of the support arm 11 or, alternatively, on the exterior thereof. The neck portion 12B of the mounting base 12 may be press fitted into or onto the tubular first end portion 11A of the support arm 11, or may be secured by an adhesive, epoxied or thermally welded to the tubular first end portion 11A of the support arm. Although the bottom flange 12A of the mounting base 12 has been illustrated as a circular configuration for purposes of example, it should be understood that the bottom flange of the mounting base may be of a generally square or rectangular configuration.

Figure 3:
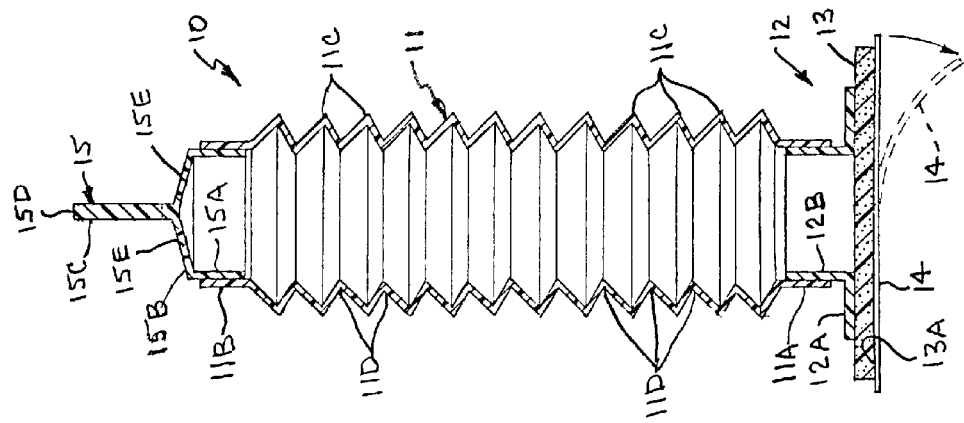
FIG. 3 is a longitudinal cross sectional view of the breathing tube support taken along line 4-4 of FIG. 2.

As best seen in FIG. 3, a flexible foam pad 13 is secured to the underside of the bottom flange 12A of the mounting base 12. The bottom surface of the foam pad 13 is covered by an adhesive layer 13A and a peel-off paper cover 14 so that the foam pad may be adhered to a patient's shoulder between the neck and the outer portion of the shoulder joint, or other location, when the cover is removed The flexible foam pad 13 may be sized to extend beyond the periphery of the bottom flange 12A of the mounting base 12 so as to conform to the curvature of the patient's shoulder or other body surface. FIG. 3 shows, in dashed line, the peel-off cover 14 partially removed from the underside of the flexible foam pad 13.

Although in a preferred mounting arrangement the foam pad 13 may be adhered to a patient's shoulder (FIG. 1), it should be understood that the foam pad may be adhered to any other convenient support surface; for example, to a flat support surface S, as shown in FIG. 2. It should also be understood that, in other mounting arrangements, the foam pad may be eliminated, and the bottom flange 12A of the mounting base 12 may be supported on a flat support surface. In other mounting arrangements the underside of the bottom flange 12A of the mounting base 12 may be provided with an adhesive layer and a peel-off paper cover 14 so that the mounting base may be adhered to a flat support surface.

The breathing tube holder member 15 is formed of a rigid or semi-rigid material having a tubular neck portion 15A at a bottom end with a top wall 15B that adjoins a vertical and laterally extending upper portion 15C extending upwardly therefrom terminating in a top edge 15D. The tubular neck portion 15A of the tube holder member 15 is sized to be received in the tubular second end portion 11B of the support arm 11 or, alternatively, on the exterior thereof. The neck portion 15A of the tube holder member 16 may be press fitted into or onto the tubular second end portion 11B of the support arm 11, or may be secured by an adhesive, epoxied or thermally welded to the tubular first end portion 11A of the support arm. The top wall 15B of the breathing tube holder member 15 may be provided with at least one aperture 15E to allow passage of air into and from the interior of the tubular support arm 11 when it is expanded (lengthened) and collapsed to prevent forming a vacuum or a pressurized condition inside the tubular support arm.

The embodiment of the breathing tube holder member 15 illustrated in FIGS. 1-7 is configured to receive and hold a pair of breathing tubes T of a conventional "dual-limb" breathing tube circuit BC (FIG. 1). A pair of laterally spaced keyhole slots 16 are formed in the upper portion 15A of the tube holder member 15 which are adapted to receive and hold a section of a respective breathing tube the breathing tube circuit. The breathing tubes of the conventional breathing tube circuit are formed of flexible extendable and collapsible corrugated plastic tubing of the type having an accordion-like construction of larger diameter ridges and smaller diameter folds Each keyhole slot 16 of the tube holder member 15 has a generally semi-circular bottom portion and a slot portion 16A extending upwardly therefrom to form an opening in the top edge 15D of the tube holder member for removably receiving the respective breathing tube. The corners of the slot portion 16A are rounded to avoid sharp surfaces which may puncture or damage the breathing tube.

The diameter of the semi-circular bottom portion of each keyhole slot 16 is slightly larger than the diameter of the smaller diameter folds of the conventional corrugated breathing tube for which it is intended, and the width of the slot portion 16A is slightly smaller than the diameter of the folds of the breathing tube, such that when the breathing tube is pressed into the keyhole slot 16, it will snap fit into the semi-circular bottom portion of the keyhole slot to retain the breathing tube therein. The larger diameter ridges of the conventional corrugated breathing tube will aid in preventing the breathing tube from sliding axially relative to the keyhole slot 16.

It should be understood, that the keyhole slots 16 may be of the same size, or may be of different sizes to accommodate breathing tubes of different diameters. It should also be understood that the tube holder member 15 may be provided with more than two keyhole slots, or, as shown in FIG. 8, that a single keyhole slot 16 may be provided to accommodate a "unilimb" breathing circuit wherein an expiratory tube and an inspiratory tube are coupled in a coaxial relation, one inside the other.

It should be understood from the foregoing, that the capability of the present breathing tube support 10 to be longitudinally extended (lengthened) and collapsed (shortened), and positioned in a bent or curved configuration, provides a wide range of adjustable positions of the breathing tubes of the breathing circuit and allows an anesthesia provider to optimally position the breathing tubes relative to the patient's head and neck area to accommodate a range of patient sizes, patient mobility, head movement, and medical procedures, etc., and to accommodate the movement of an intubated patient, while maintaining relative position of the breathing tubes regardless of the position of the patient, and thereby minimize forces applied to an endotracheal tube and the risk of injury to the intubated patient.

While the present invention has been disclosed in various preferred forms, the specific embodiments thereof as disclosed and illustrated herein are considered as illustrative only of the principles of the invention and are not to be considered in a limiting sense in interpreting the claims. The claims are intended to include all novel and non-obvious combinations and sub-combinations of the various elements, features, functions, and/or properties disclosed herein. Variations in size, materials, shape, form, function and manner of operation, assembly and use, are deemed readily apparent and obvious to one skilled in the art from this disclosure, and all equivalent relationships to those illustrated in the drawings and described in the specification are intended to be encompassed in the following claims defining the present invention.

The invention claimed is:

1. A breathing tube support device that attaches to a patient or a support surface for holding and supporting at least one flexible breathing tube of a breathing circuit during provision of anesthesia, assisted and artificial ventilation, and/or spontaneous ventilation, comprising:
   a flexible support arm formed of a length of flexible axially extendable and collapsible accordion-like corrugated tubing having alternating ridges and folds that are expandable and collapsible;
   a mounting base at a bottom end of said flexible support arm for attachment to the patient or support surface;
   a breathing tube holder member at a top end of said flexible support arm having an upper portion extending vertically upward and laterally outward from said top end of said flexible support arm terminating in a top edge, and at least one aperture formed in said upper portion for receiving, and releasably engaging a section of the at least one flexible breathing tube of the breathing circuit in a snap fit relation to releasably retain and support the at least one flexible breathing tube; and
   said flexible support arm being expanded to increase its length longitudinally and collapsed upon itself to shorten its length longitudinally, and being sufficiently flexible to assume a bent or curved configuration, and sufficiently stable to retain said bent or curved configuration, whereby the at least one flexible breathing tube of the breathing circuit held and supported thereby is optimally positionable relative to the patient's head and neck area.

2. The breathing tube support device according to claim 1, wherein
   said mounting base has a bottom flange portion;
   a flexible foam pad secured an underside of said flange portion;
   an adhesive layer on an underside of said flexible foam pad covered by a removable peel-off cover; wherein
   said foam pad sized and shaped and sufficiently flexible so as to conform to and adhere to a support surface selected from the group consisting of a shoulder of the patient, a body surface of the patient, and a flat support surface, when said cover is removed.

3. The breathing tube support device according to claim 2, wherein
   said foam pad is sized and shaped and sufficiently flexible so as to conform and adhere to the curvature of a shoulder of the patient.

4. The breathing tube support device according to claim 1, wherein
   said mounting base has a bottom flange portion;
   an adhesive layer on an underside of said bottom flange portion covered by a removable peel-off cover; wherein
   said bottom flange portion is sized and shaped to and adhere to a flat support surface when said cover is removed.

5. The breathing tube support device according to claim 1, wherein
   said at least one aperture of said breathing tube holder member comprises a generally keyhole-shaped aperture formed in said upper portion having a generally semi-circular bottom portion and a slot portion extending upwardly therefrom to form an opening in said top edge;
   said slot portion having a width slightly smaller than the diameter of said generally semi-circular bottom portion such that when the at least one flexible breathing tube of the breathing circuit is pressed into said slot portion, it will snap fit into said generally semi-circular bottom portion of said generally keyhole-shaped aperture to retain and support the breathing tube therein.

6. The breathing tube support device according to claim 5, wherein the at least one flexible breathing tube of the breathing circuit is formed of flexible axially extendable and collapsible accordion-like corrugated tubing having alternating larger diameter ridges smaller diameter folds; and said slot portion of said at least one generally keyhole-shaped aperture of said breathing tube holder member has a width slightly smaller than the smaller diameter folds such that when the at least one flexible breathing tube of the breathing circuit is pressed into said slot portion, a smaller diameter fold will snap fit into said generally semi-circular bottom portion of said generally keyhole-shaped aperture to retain and support the breathing tube therein.

\* \* \* \* \*